Figure 3B:
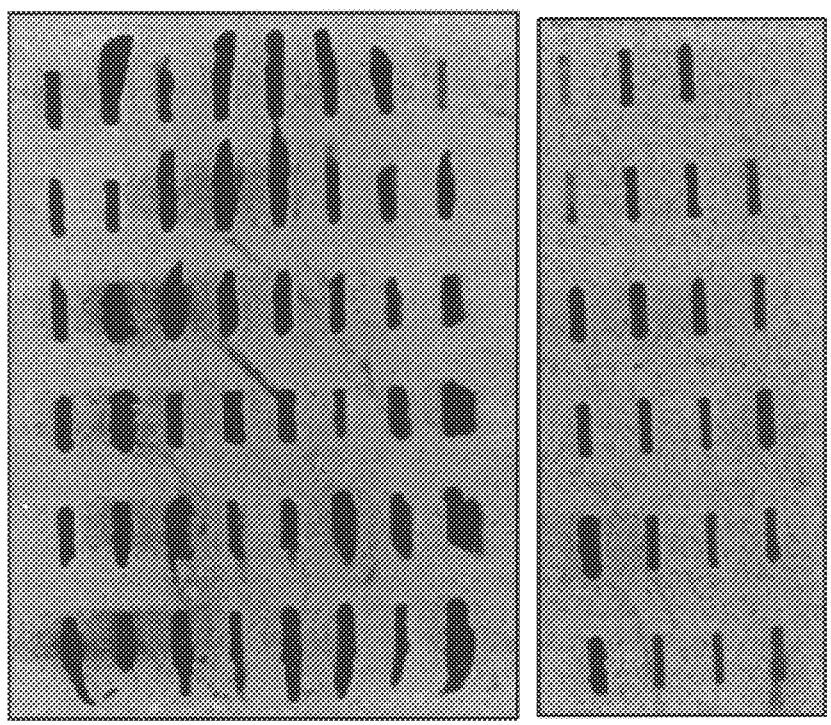

United States Patent [19]
Plowman

[11] Patent Number: 5,830,648
[45] Date of Patent: Nov. 3, 1998

[54] ASSAY AND METHOD FOR TRANSCRIPT IMAGING

[75] Inventor: Gregory D. Plowman, San Carlos, Calif.

[73] Assignee: Sugen, Inc., Redwood City, Calif.

[21] Appl. No.: 436,065

[22] Filed: May 5, 1995

[51] Int. Cl.$^6$ .............................. C12Q 1/68; C12P 19/34; C07H 21/04
[52] U.S. Cl. ......................... 435/6; 435/91.2; 536/24.33
[58] Field of Search ........................ 435/6, 172.1, 172.3, 435/91.2; 536/23.2, 24.3, 24.31, 24.33

[56] References Cited

U.S. PATENT DOCUMENTS 4,800,159  1/1989  Mullis et al. ........................... 435/91.2

OTHER PUBLICATIONS

Biesecker, Leslie G., et al. "Identification of four murine cDNAs encoding putative protein kinases from primitive embryonic stem cells differentiated in vitro". *Proc. Natl. Acad. Sci. USA* 90:7044–7048 (1993).
Bishop, Michael J. "The Molecular Genetics of Cancer", *Science* 235:305–311 (1987).
Cance, William G., et al. "Novel Protein Kinases Expressed in Human Breast Cancer", *Int. J. Cancer* 54:571–577 (1993).
Elder, James T., et al. "Overexpression of Transforming Growth Factor α in Psoriatic Epidermis". *Science* 243:811–814 (1989).
Feng, Gen–Sheng, et al. "SH2–Containing Phosphotyrosine Phosphates as a Target of Protein–Tyrosine Kinases", *Science* 259: 1607–1611 (1993).
Fry, David W. "Protein tyrosine kinases as therapeutic targets in cancer chemotherapy and recent advances in the development of new inhibitors". *Exp. Opin. Invest. Drugs* 3(6):577–595 (1994).
Hanks, Steven K., et al. "The Protein Kinase Family: Conserved Features and Deduced Phylogeny of the Cataytic Domains", *Science* 241:42–52 (1988).
Hynes, N.E. and Stern, D.F. "The Biology of erbB–2/neu/HER–2 and it Role in Cancer", *Biochim Biophys Acta* 1198:165–184 (1994).
Krueger, Neil X., et al. "Structural diversity and evolution of human receptor–like protein tyrosine phosphates". *The EMBO Journal* 9(10):3241–3252 (1990).
Lai, Cary and Lemke, Greg "An Extended Family of Protein–Tyrosine Kinase Genes Differentially Expressed in the Vertebrate Nervous System". *Neurön* 6:691–704 (1991).
Levitzki, Alexander and Gazit, Aviv "Tyrosine Kinase Inhibition: An Approach to Drug Development". *Science* 267:1782–1788 (1995).
Maher, Pamela A. and Pasquale, Elena B. "Tyrosine Phosphorylated Proteins in Different Tissues during Chick embryo Development", *The Journal of Cell Biology* 106:1747–1755 (1988).
Marcella, C. and Eichmann A. "Molecular cloning of a family of protein kinase genes expressed in the avian embryo". *Oncogene* 7:2479–2487 (1992).
Ninfa, Elizabeth G. and Dixon, Jack E. "Protein tyrosine phosphates in disease processes". *Trends in Cell Biology* 4:427–430 (1994).
Pasquale, Elena B. "A distinctive family of embryonic protein–tyrosine kinase receptors". *Proc. Natl. Acad. Sci USA* 87:5812–5816 (1990).
Partanen, Juha, et al. "Putative tyrosine kinases expressed in K–562 human leukemia cells". *Proc. Natl. Acad. Sci. USA* 87:8913–8917 (1990).
Ross, Russell "Platelet–Derived Growth Factor". *The Lancet* 1179–1182 (1989).
Sahin, Mustafa and Hockfield, Susan "Protein Tyrosine Photophatases Expressed in the Development Rat Brain". *The Journal of Neuroscience* 13(11):4968–4978 (1993).
Saiki, Randall K., et al. "Primer–Directed Enzymatic Amplification of DNA with a Thermostable DNA Polymerase". *Science* 239:487–491 (1988).
Saiki, Randall K., et al. "Enzymatic Amplification of β–Globin Genomic Sequences and Restriction Site Analysis for Diagnosis of Sickle Cell Anemia". *Science* 230:1350–1354 (1985).
Sanchez, Marina P., et al. "Multiple tyrosine protein kinases in rat hippocampal neurons: Isolation of Ptk–3, a receptor expressed in proliferative zones of the developing brain". *Proc. Natl. Acad. Sci. USA* 1891:819–1823 (1994).
Schepens, Jan, et al. "Identification and typing of members of the protein–tyrosine phosphatase gene family expressed in mouse brain". *Molecular Biology Reports* 16:241–248 (1992).
Schlesinger, J. and Ullrich, A. "Growth Factor Signaling by Receptor Tyrosine Kinases". *Neuron* 9:383–391 (1992).
Shen, Shi–Hsiang, et al. "A protein–tyrosine phosphatase with sequence similarity to the SH2 domain of the protein–tyrosine kinases". *Nature* 352:736–739 (1991).
Shock, Lisa P., et al. "Protein tyrosine phosphatases expressed in developing brain and retinal Müller glia". *Molecular Brain Research* 28:110–116 (1995).
Siyanova, E.Y., et al. "Tyrosine kinase gene expression in the mouse small intestine". *Oncogene* 9:2053–2057 (1994).
Tonks, Nicholas K., et al. "Purification of the Major Protein–tyrosine phosphatases of Human Placenta". *The Journal of Biological Chemistry* 263(14):6722–6730 (1988).
Vassar et al. "Transgenic mice provide new insights into the role of TGF–α during epidermal development and differentiation", *Genes and Development* 5:714–727 (1991).

(List continued on next page.)

*Primary Examiner*—George C. Elliott
*Assistant Examiner*—John S. Brusca
*Attorney, Agent, or Firm*—Pennie & Edmonds LLP

[57] ABSTRACT

The invention is directed to assays and methods for transcript imaging. More particularly, the invention is directed to assays and methods for detecting, determining and quantifying the expression level of all known biomolecules in a family of biomolecules, including tyrosine kinases, tyrosine phosphatases and serine/threonine kinases, in uncharacterized biological samples, regardless of species. Such assays and methods may be used as a diagnostic, therapeutic and/or a research tools.

30 Claims, 6 Drawing Sheets

OTHER PUBLICATIONS

Vogel et al. "Activation of a Phosphototyrosine Phosphatase by Tyrosine Phosphorylation". *Science* 259:1611–1614 (1993).

Wilks et al. "The application of the polymerase chain reaction to cloning members of the protein tyrosine kinase family". *Gene.* 85:67–74 (1989).

Wilks. "Two putative protein–tyrosine kinases identified by application of the polymerase chain reaction". *Proc. Natl. Acad. Sci. USA* 86:1603–1607 (1989).

Yang et al. "Isolation of a cDNA clone encoding a human protein–tyrosine phosphatase with homology to the cytoskeletal–associated proteins band 4.1, ezrin, and talin". *Proc. Natl. Acad. Sci USA* 88:5949–5953 (1991).

Guersen et al. Population study of T cell receptor V–beta gene usage in peripheral blood lymphocytes: differences in ethnic groups Clin. Exp. Immunol. vol. 94 201–207, 1993.

Werner et al. Experimental diabetes increases insulinlike growth factor I and II receptor concentration and gene expression in kidney Diabetes vol. 39 1490–1497, 1990.

Ikeda et al. Expression and functional role of the proto–oncogene c–kit in acute myeloblastic leukemic cells Blood vol. 78 2962–2968, 1991.

Boehm Analysis of multigene families by DNA fingerprinting of conserved domains: directed cloning of tissue–specific protein tyrosine phosphatases Oncogene vol. 8 1385–1390, 1993.

Caldwell et al. Surface and cytoplasmic expression of CD45 antigen isoforms in normal and malignant myeloid cell differentiation Am. J. Hematol. vol. 95 180–187, 1991.

Cohen et al. Interleukin 6 induces myeloid differentiation of a human biphenotypic leukemic cell line Leukemia Research vol. 16 751–760, 1992.

Hendriks et al. Rapid assessment of protein–tyrosine phosphatase expression levels by RT–PCR with degenerate primers. Mol. Biol. Reports vol. 19 105–108, 1994.

Marguerie et al. PCR–based analysis of the TCR repertiore in human autoimmune diseases. Immunology Today vol. 13 pp. 336–338, 1992.

FIG. 1A

TYROSINE PHOSPHATASE TRANSCRIPT IMAGING

| OLIGO NAME | OLIGO NUMBER | SEQUENCE (IUPAC CODE) | ID |
|---|---|---|---|
| PTPDFW | (3002) | GAYTTYTGGVRNATGRTNTGGGA | DFW$MVWE |
|  |  | $=SKNRQHREDGC | M |
| PTPHCSA-T | (3003) | CGGCCSAYNCCNGCNSWRCARTG | R V HCSAGIGR Y M F |

FIG. 1B-1

TYROSINE KINASE "RTK" TRANSCRIPT IMAGING

| OLIGO NAME | AA ENCODED | MOTIF | REPRESENTATION | |
|---|---|---|---|---|
| HRDRTK | M V K I IHRDLA L S V Q F H | "HRDLA" "HRDIA" "HRDVA" "HKDLA" | 66 4 1 4 | (LTK, ALK, FAK, PYK2) (CSF1R) (RYK, CCK4, ROR1, ROR2) |
| HRDH3a | S F VHRNLA | "HRNLA" | 1 | (HER3) |
| HRDIAFAK | V K IHRDIA L S Q H | "HRDIA" | 4 | (LTK, ALK, FAK, PYK2) |
| DVWSRTK | RY I DVWSFGV T M C W | "DVWS" "DMWS" * "DVWM" * | 66 1 2 | (INSR) (FAK, PYK2) |
| DSWLTKb | R R DSWSLGI T T C C W W | "DSWS" "DTWS" "DTWM" | 1 1 1 | (LTK) (ALK) (ACK) |

FIG. 1B-2

```
              R
DAWST11    DAWSYGV      "DAWS"    1  (TYRO11/HTK)
              T
              C
              W

RY I
DIWSRTK    DIWSFGV      "DIWS"    2  (ROR1, ROR2)
              T  M      "DIWA" *  1  (BTK)
              C
              W

DVWAFAK    DVWAFGV      "DVWA"   10  (CCK4, MER, TYRO3, DDR, TYRO10,
                                      RYK, TORP, MKK2, ABL, ARG)
                        "DVWM" *  2  (FAK, PYK2)

DTWMPYK1   DTWAFGV      "DTWM" *  1  (ACK)

V S FS
HRDSRC     IHRDLR       "HRDLR"   9  (SRC-FAMILY)
              M

M
           V K IK
HRDA3      IHRDLN       "HRDLN"   2  (ASTRO3, LIMK)
           L S V
              Q F
              H

RY I
DVWSRTK    DVWSFGV      "DVWS"   66
              T  M      "DMWS" *  1  (INSR)
              C         "DVWM" *  2  (FAK, PYK2)
              W

RY I
DIFSA3     DVFSFGV      "DVFS"    1  (LIMK)
              T  M      "DIFS" *  1  (AS TRO3)
              C
              W

* = NON-EXACT MATCH
```

FIG. 2
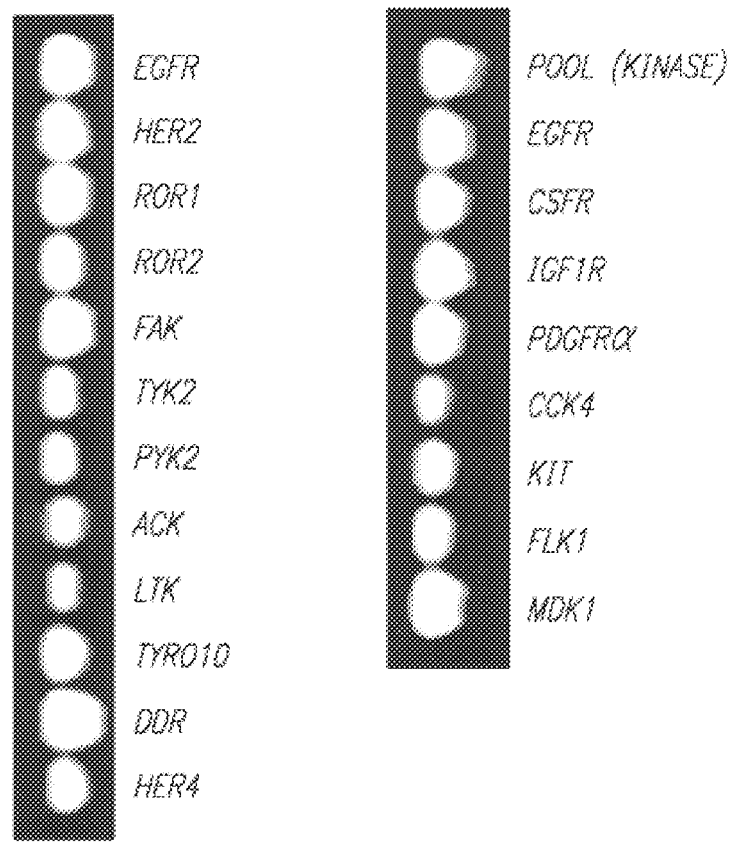
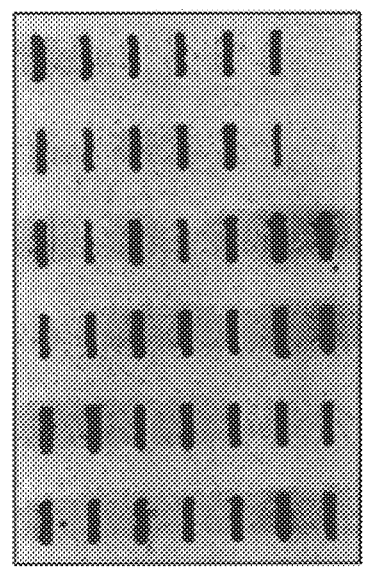
FIG. 3A

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: unknown ( D ) TOPOLOGY: unknown ( i i ) MOLECULE TYPE: protein ( x i ) SEQUENCE DESCRIPTION: SEQ ID NO:1:

Trp  Met  Ala  Pro  Glu  Ala
    1                   5

( 2 ) INFORMATION FOR SEQ ID NO:2:

( i ) SEQUENCE CHARACTERISTICS:
          ( A ) LENGTH: 6 amino acids
          ( B ) TYPE: amino acid
          ( C ) STRANDEDNESS: unknown
          ( D ) TOPOLOGY: unknown ( i i ) MOLECULE TYPE: protein ( x i ) SEQUENCE DESCRIPTION: SEQ ID NO:2:

Trp  Met  Ser  Pro  Glu  Ala
    1                   5

( 2 ) INFORMATION FOR SEQ ID NO:3:

( i ) SEQUENCE CHARACTERISTICS:
          ( A ) LENGTH: 6 amino acids
          ( B ) TYPE: amino acid
          ( C ) STRANDEDNESS: unknown
          ( D ) TOPOLOGY: unknown ( i i ) MOLECULE TYPE: protein ( x i ) SEQUENCE DESCRIPTION: SEQ ID NO:3:

Trp  Met  Ala  Leu  Glu  Ser
    1                   5

( 2 ) INFORMATION FOR SEQ ID NO:4:

( i ) SEQUENCE CHARACTERISTICS:
          ( A ) LENGTH: 36 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:4:

CCGGGATCCA CAAGCTTCCC TNCAYMRDGA YNTNGC                                                      36

( 2 ) INFORMATION FOR SEQ ID NO:5:

( i ) SEQUENCE CHARACTERISTICS:
          ( A ) LENGTH: 36 base pairs
          ( B ) TYPE: nucleic acid
          ( C ) STRANDEDNESS: unknown
          ( D ) TOPOLOGY: unknown ( i i ) MOLECULE TYPE: DNA (genomic)

( x i ) SEQUENCE DESCRIPTION: SEQ ID NO:5:

CCGGGATCCA CAAGCTTCCG TNCAYMGNAA YYTNGC                                                      36

( 2 ) INFORMATION FOR SEQ ID NO:6:

( i ) SEQUENCE CHARACTERISTICS:
          ( A ) LENGTH: 36 base pairs
          ( B ) TYPE: nucleic acid
          ( C ) STRANDEDNESS: unknown
          ( D ) TOPOLOGY: unknown (  i  i  ) MOLECULE TYPE: DNA (genomic)

(  x  i  ) SEQUENCE DESCRIPTION: SEQ ID NO:6:

CCGGGATCCA CAAGCTTCCC TNCAYMRDGA YATHGC                36

( 2 ) INFORMATION FOR SEQ ID NO:7:

(  i  ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:7:

CCGGGATCCA CAAGCTTCCR TNCAYMGNGA YYTNMG                36

( 2 ) INFORMATION FOR SEQ ID NO:8:

(  i  ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:8:

CCGGGATCCA CAAGCTTCCC TNCAYMRDGA YNTNAA                36

( 2 ) INFORMATION FOR SEQ ID NO:9:

(  i  ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:9:

CCGAATTCAC AAGATCTCCC AYNCCRWANS WCCANACRTC                40

( 2 ) INFORMATION FOR SEQ ID NO:10:

(  i  ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:10:

CCGAATTCAC AAGATCTCCD ATNCCRAANS WCCANSWRTC                40

( 2 ) INFORMATION FOR SEQ ID NO:11:

(  i  ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:11:

CCGAATTCAC AAGATCTCCN ACNCCRTANS WCCANGCRTC                40

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

CCGAATTCAC AAGATCTCCC AYNCCRWANS WCCADATRTC      40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

CCGAATTCAC AAGATCTCCN ACNCCRAANG CCCANACRTC      40

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

CCGAATTCAC AAGATCTCCN ACNCCRAANG CCCANGTRTC      40

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

CCGAATTCAC AAGATCTCCC AYNCCRWANS WCCANACRTC      40

( 2 ) INFORMATION FOR SEQ ID NO:16:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

CCGAATTCAC AAGATCTCCC AYNCCRWANS WRAANACRTC      40

( 2 ) INFORMATION FOR SEQ ID NO:17:

( i ) SEQUENCE CHARACTERISTICS:

(A) LENGTH: 23 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:17:

GAYTTYTGGV RNATGRTNTG GGA 23

(2) INFORMATION FOR SEQ ID NO:18:

(i) SEQUENCE CHARACTERISTICS:
(A) LENGTH: 23 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:18:

CGGCCSAYNC CNGCNSWRCA RTG 23

(2) INFORMATION FOR SEQ ID NO:19:

(i) SEQUENCE CHARACTERISTICS:
(A) LENGTH: 40 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:19:

CCGAATTCAC AAGATCTCCN ACNCCNARNS WCCANACRTC 40

(2) INFORMATION FOR SEQ ID NO:20:

(i) SEQUENCE CHARACTERISTICS:
(A) LENGTH: 40 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:20:

CCGAATTCAC AAGATCTCCC AYNCCRWANG CCCADATRTC 40

(2) INFORMATION FOR SEQ ID NO:21:

(i) SEQUENCE CHARACTERISTICS:
(A) LENGTH: 40 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:21:

CCGAATTCAC AAGATCTCCN ACNCCRAANS WCCACATRTC 40

ASSAY AND METHOD FOR TRANSCRIPT IMAGING

TABLE OF CONTENTS
1. INTRODUCTION
2. BACKGROUND OF THE INVENTION
3. SUMMARY OF THE INVENTION
4. DESCRIPTION OF THE DRAWINGS
5. DETAILED DESCRIPTION OF THE INVENTION
    5.1. Detection And Quantification Of Members Of Biomolecule Families
    5.2. Application Of The Claimed Methods
6. EXAMPLE
    6.1. Transcript Imaging "Pool" Control For Determining PTP Expression Levels
    6.2. Transcript Imaging To Determine PTKs Expression Levels
    6.3. Additional Control Experiment
CLAIMS

1. INTRODUCTION

The present invention is directed to assays and methods for simultaneously detecting, assessing and quantifying the expression levels of all known members of a family of biomolecules in a biological sample, regardless of the sample's origin (e.g. species, sample source). For example, the invention is directed to the detection, assessment and quantification of all known tyrosine kinases, tyrosine phosphatases, and/or serine/threonine kinases in a biological sample.

2. BACKGROUND OF THE INVENTION

The development and survival of multicellular organisms depends on the coordinated regulation of specific cellular interactions. These interactions are often mediated by secreted proteins such as growth factors or ligands which recognize specific binding sites, including receptors on the surface of cells. The binding event between these proteins and their specific binding site initiates a cascade of biochemical events which ultimately reaches the nucleus, resulting in modulation and regulation of gene expression. The combined activities of the proteins encoded by these genes determines the biological outcome of this elaborate cascade, e.g. biological effects such as cell survival and growth, migration, differentiation or metabolism.

With respect to binding events between a protein and its specific receptor, several families of the cell surface receptors involved in the cascade have been identified, including receptor tyrosine kinases (RTKs), serine/threonine kinase receptors, G-protein-coupled receptors, interleukin-, interferon-, and other cytokine receptors, ligand-gated ion channels, guanylyl cyclases, and chemokine receptors.

One of the most abundant families of cell surface receptors involved in the regulation of cell growth and survival, differentiation, migration and metabolism are the RTKs, represented by at least nineteen (19) subfamilies. A common feature of all RTKs is their intrinsic tyrosine kinase activity which, upon activations by the binding of a specific ligand or growth factor, catalyzes the tyrosine phosphorylation of a variety of cellular substrate molecules. For review, please see, Ullrich and Schlessinger, 1990, *Cell* 61:203–212; Schlessinger and Ullrich, 1992, *Neuron* 9:383–391. A growing body of evidence suggests that tyrosine phosphorylation of cellular proteins is involved in a substantial number of key physiological functions, as evidenced by the very distinct and well-defined protein tyrosine kinase phosphorylation patterns found during embryonic development and in adult human tissue. Maher and Pasquale, 1988, *J. Cell. Biol.* 106:1747–1755; Pasquale, 1990, *Proc. Natl. Acad. Sci. USA* 87:5812–5816. In addition to the RTKs there exist at least ten (10) subfamilies of non-receptor tyrosine kinases that lack a transmembrane domain and reside as intracellular proteins. Although lacking direct access to the extracellular environment, these non-receptor tyrosine kinases can be activated by associating with numerous receptor-mediated signal transduction pathways. The superfamily of all (receptor and non-receptor) proteins comprising tyrosine kinase activity has been designated as protein tyrosine kinases (PTKs).

A second family of proteins, designated protein tyrosine phosphatases (PTPs), has been identified and is believed to act in concert with RTKs in order to modulate the tyrosine phosphorylation of cellular substrates by removal of phosphate residues. Tonks et al., 1988, *J. Biol. Chem.* 263:6722–6730. The level of tyrosine phosphorylation is determined by the balance between the activities of tyrosine kinases and phosphatases, as such the balanced activity of these two protein families happens to be highly critical for the disease-free survival of the multicellular organism. As in the case of tyrosine kinases, tyrosine phosphatases exist as both receptor and non-receptor proteins.

The pivotal signals regulated by PTKs and PTPs require a tight spatial and temporal control. Imbalances in the cellular tyrosine phosphorylation level have been linked to a variety of metabolic and proliferative diseases. For example, abnormalities in the insulin receptor-mediated signal transduction results in the metabolic disease diabetes mellitus. As a further example, in neuronal cells, the impairment of growth factor stimulated tyrosine kinase signal transduction results in the onset of apoptosis and programmed cell death. Overexpression of tyrosine kinase or impaired tyrosine phosphatase function may also be detrimental. For example, increased tyrosine phosphorylation has been associated with proliferative diseases such as cancer (see e.g., Bishop, 1987, *Science* 335:305–311), atherosclerosis (Ross, 1989, *Lancet* 1:1179–1182), and probably psoriasis (Elder et al., 1989, *Science* 243:811–814; Vassar et al., 1991, *Gene & Dev.* 5:714–727).

Direct correlation of increased tyrosine phosphorylation and particular pathological conditions has been demonstrated in an array of specific instances. For example, in mammary carcinoma and ovarian carcinoma, the amplification of the neu/HER2/c-erbB2 proto-oncogene has been found to be the hallmark of the disease in 30% of the cases. The degree of the amplification of the proto-oncogene and the overexpression of its protein product were found to correlate with the severity of disease and poor prognosis. Slamon et al., 1989, *Science* 244:707–712. In addition, the overexpression of other PTKs, including the PDGF-R, EGF-R, HER3, and others, have been shown to correlate with specific subsets of cancer. See e.g., Plowman et al., 1994, *DN & P* 7:334–339.

The central role of tyrosine phosphorylation in cellular proliferation suggests that a means to monitor the relative expression of these molecules in specific cell lineages, or in normal tissue versus diseased tissues may be of significant diagnostic, therapeutic, or scientific utility.

For purposes of this Application and as more fully discussed in the "Detailed Description" section, infra, "diagnostics" generally refers to the evaluation of the expression pattern of one or more members of a family of biomolecules for the purpose of, for example, identifying a disease state by the abnormal expression of such member(s) of the specific biomolecule family. The term "therapeutic" generally refers to methods which may enable the implementation of a targeted drug therapy where a drug is rationally selected from a panel of kinase and phosphatase-specific inhibitors based on the sample tissue or cell culture's PTK and/or PTP expression profile. "Research" applications include the imaging of samples to identify cell lines whose profile is most similar to a specific primary cell or diseased cell population, which can be used as experimental disease model. Further research applications involve the identification of known or unknown molecules associated with the development of certain pathological disorders.

There are presently more than ninety (90) known mammalian PTKs and more than forty (40) known PTPs. Within their catalytic domains, each family conserves distinct amino acid residues (Hanks et al., 1988, *Science* 241:42–52; Krueger et al., 1990, *EMBO J.* 9:3241–3252; Yang & Tonks, 1991, *Proc. Natl Acad. Sci.* 88:5949–53). These conserved protein motifs have recently been exploited using PCR-based cloning strategies leading to a significant expansion of the known kinases and phosphatases. Wilks, 1989, *Genetics* 86:1603–1607; Wilks et al., 1989, *Gene* 85:67–74; Yang & Tonks, supra; Schepens et al., 1992, *Mol. Biol. Reports* 16:241–248; Sahin et al., 1993, *J. Neurosci.* 13:4968–4978; Shuck et al., 1995, *Mol. Brain Res.* 28:110–116.

Generally, PCR, or polymerase chain reaction, is the enzymatic amplification of sequences residing between two oligonucleotide primers that define the 5' and 3' borders of the nucleotide sequence to be amplified. Saiki et al., 1985, *Science* 230:1350–1354; Saiki et al., 1988, *Science* 239:487–491, U.S. Pat. No. 4,800,159.

PCR-based cloning strategies have been used to identify protein tyrosine kinases from diverse biological samples including specific hematopoietic cell types (Wilks, 1989, *Genetics* 86:1603–1607), neuronal tissue (Lai and Lemke, 1991, *Neuron* 6:691–704), leukemia cell lines (Partanen et al., 1990, *Proc. Natl. Acad. Sci. USA* 87:8913–8917), and embryonic tissue (Millauer et al., 1993, *Cell* 72:835–846; Marcelle and Eichmann, 1992, *Oncogene* 7:2479–2487).

An analogous strategy has been developed for the identification and isolation of a variety of PTKs from human breast cancer cells (Vogel et al., 1993, *Science* 259:1611–1614) and other origins (Feng et al., 1993, *Science* 259:1607–1611; Shen et al., 1991, *Nature* 352:736–739). Most all of these cloning strategies have employed a pair of degenerate oligonucleotides designed according to the conserved regions in the catalytic domains of PTKs or PTPs, respectively, for the amplification of single stranded cDNA synthesized from the targeted source.

These protocols, however, result in the biased amplification of a subset of PTKs or PTPs, respectively, while other PTKs or PTPs are under-represented in the pool of amplification products. Thus, although currently known strategies may be employed for the qualitative determination of PTK/PTP expression patterns and the identification of novel members of such gene families, they are not useful for the simultaneous quantitative evaluation of expression profiles. A related strategy uses non-degenerate primers for quantitative assessment of RNA abundance. However, such a strategy is species-dependent, such that knowledge regarding, for example a rat PTK, would not generally be applicable to determining the expression level of the corresponding human PTK.

For example, Cance et al., 1993, *Int. J. Cancer* 54:571–577 used the above-described PCR cloning technique based on consensus sequences within the kinase domain (Wilks, supra; Lai and Lemke, supra) to identify the protein tyrosine kinases expressed in the human breast cancer cell line 600PEI. Subsequent to the identification of a spectrum of 21 different known and novel PTKs, Cance discussed the determination of expression levels of the so identified members of the PTK family in a panel of primary and metastatic human breast carcinomas. Specifically, Cance et al. designed non-degenerate oligonucleotide primers for each of the twenty-one (21) PTKs, followed by calibration of the system to the levels of actin expression in each tumor. However, though this technique of expression PCR developed by Cance et al., supra, allows the semi-quantitative evaluation of expression levels of specific PTKs in precharacterized cell lines or tissues, this approach does not allow the evaluation of expression patterns and identification of abnormal expression profiles in yet uncharacterized tissue- and cell types.

3. SUMMARY OF THE INVENTION

The present invention relates to an assay for simultaneously detecting and quantifying the expression of any known member of a family of biomolecules in a sample. More specifically, the present invention relates to an assay for rapidly detecting and quantifying the expression of known PTKs, PTPs and/or serine/threonine kinases in a sample. For purposes of this specification, the term "quantify" shall include determining the relative abundance of RNA transcript for each specific member of the PTK, PTP and/or serine/threonine kinase family in a sample.

The present invention further relates to a method for simultaneously detecting and quantifying the expression of biomolecules in a sample. In one embodiment, the present invention relates to a method for detecting and quantifying the expression of known PTKs, PTPs and/or serine/threonine kinases in a sample.

The present invention also is directed to the use of the claimed methods and assays for diagnostic, therapeutic or alternatively, research purposes.

Unlike the methods described above in the "Background" section, infra, the PCR based assays described herein, using degenerate oligonucleotide primer pools, allow for the amplification of all known biomolecules in a family of biomolecules, for example, PTKS, PTPs or serine/threonine kinases, with the same efficiency. Moreover, the methods disclosed are sensitive enough to allow the evaluation of limited amounts of sample, such as selected primary cells, cryostat sections of diseased tissues derived, for example, from biopsies or even single cells. Since the degenerate oligonucleotide pools employed are species-independent, the methods and assays of the present invention, unlike the methods of the prior art, allow for the identification and quantification of specific members of a family of biomolecules, such as PTKs, PTPs and/or serine/threonine kinases, whose human counterpart has not yet been cloned and characterized.

4. DESCRIPTION OF THE DRAWINGS

FIG. 1A sets forth the peptide sequences (SEQ ID NO:17 and SEQ ID NO:18) used for PTP amplification in the "Examples" section of this Specification.

FIGS. 1B and 1C set forth the peptide sequences used for PTK amplification in the "Examples" section of this Specification.

FIG. 2 depicts a control PCR against PTK plasmids. The PTK oligonucleotide primer pool was used to amplify the corresponding regions of 10 ng of various PTK plasmids as indicated. The amplification product was separated by agarose gel electrophoresis, the DNA bands visualized by ethidium bromide staining and UV light.

FIGS. 3A and 3B: "Pool" Controls for PTPs and PTKs. FIG. 3A depicts a control blot for PTP Transcript Imaging wherein a mix of equal molar amounts of all PTP plasmid DNAs was primed with the PTP oligonucleotide pool described herein, the amplification product labeled with $^{33}$P-dCTP and hybridized against slot blots on nylon membranes containing equal molar amounts of the different PTP DNAs. FIG. 3B corresponds to a control blot for PTK transcript imaging.

Figure 4A:
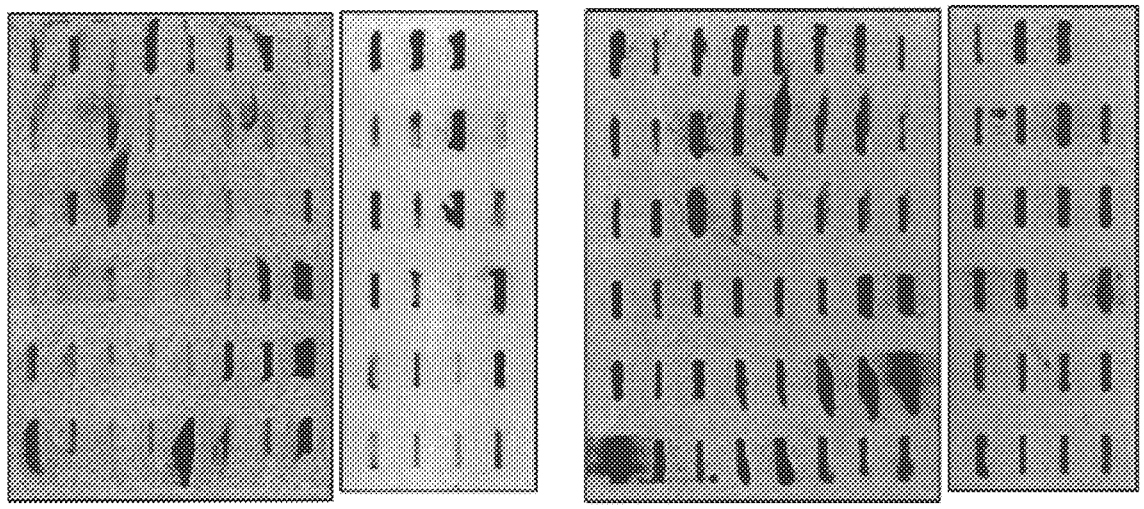
Figure 4B:
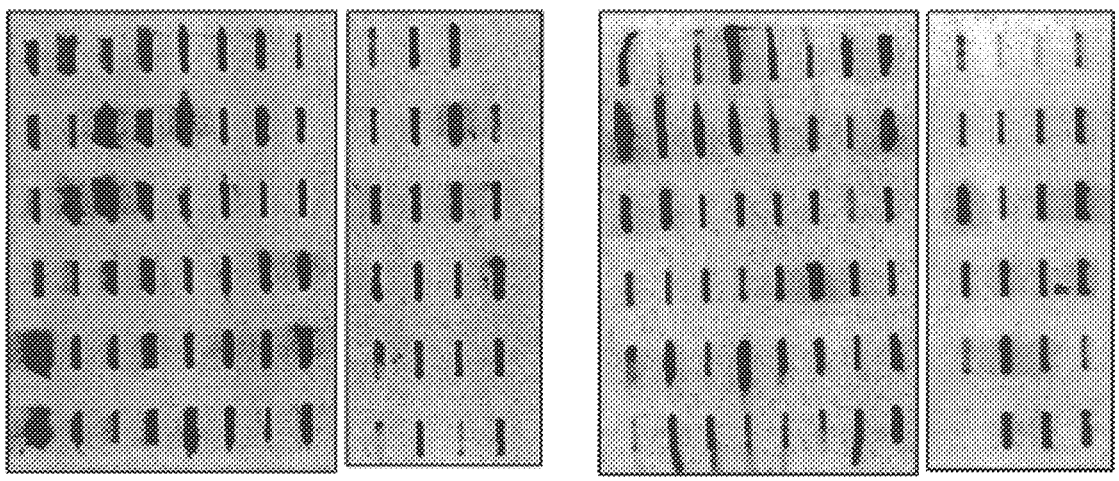

FIGS. 4A and 4B. Transcript Imaging For Tyrosine Kinases. FIGS. 4A and 4B depict PTK Transcript Imaging in a human breast epithelial cell line, HBL100, a human epidermoid carcinoma cell line, A431, and two (2) human breast adeno carcinoma cell lines, SKBR3 and BT474.

5. DETAILED DESCRIPTION OF THE INVENTION

The assays, methods and techniques of the present invention may be applied to assess the expression level of all known members of a family of biomolecules wherein such family may be characterized by at least one conserved amino acid region or "motif". Thus, a sample may be assessed and the expression levels of each known member of a family of biomolecules, including PTKs, PTPs, serine/threonine kinases, SH2, SH3, the interleukin-, interferon-, and other cytokine receptors, ligand-gated ion channels, guanylyl cyclases, chemokine receptors, enzymes and ligands such as neurotrophins, and steroid hormone receptors, may be determined according to the methods and assays described herein.

In one aspect of the present invention, the methods and assays may be used to determine the expression of PTKs, PTPs and serine/threonine kinases. With respect to these molecules, at present, approximately ninety (90) mammalian PTKs, forty (40) PTPs and at least twelve (12) serine/threonine kinases have been isolated and characterized. Each family (PTK, PTP and serine/threonine kinase) may be characterized by distinct regions of conservation in their catalytic domain.

The present invention exploits these conserved motifs using PCR based cloning strategies to detect and quantify the expression profile of a specific family of biomolecules (e.g. PTK, PTP and/or serine/threonine kinase) from diverse biological samples, including neuronal or hematopoietic cell types, embryonic cells or tissues, and tumors from any species. The present invention is sufficiently sensitive that small amounts of sample, including primary cells, cryostat sections of diseased tissue or even a single cell, may be evaluated.

5.1. Detection And Quantification Of Members Of Biomolecule Families

Preparation Of Oligonucleotide Primers

In order to simultaneously detect and quantify the expression levels of biomolecules, including PTKs, PTPs and serine/threonine kinases in a biological sample from any source using PCR techniques, at least two problems must be resolved with respect to an appropriate oligonucleotide primer set: (1) preparation of a representative set of oligonucleotides such that each known biomolecule is represented; and (2) determination of a representative set of oligonucleotides such that the amplification of each known biomolecule accurately reflects the level of expression of that specific biomolecule in the test sample.

In order to resolve these problems, conserved regions within the family of biomolecules first are determined and aligned using available means. More specifically, the regions which would allow PCR amplification of all known members of the biomolecule family are determined by, among other means, conducting an exhaustive search of all publicly available databases to identify known sequences for the biomolecules and collecting all relevant information in a single database.

The relevant regions of these biomolecules, for example, the catalytic regions of the known PTKs, PTPs and serine/threonine kinases, are then subjected to one or more means for aligning the relevant regions, including alignment programs as described in, for example *Nucleic Acids Research*, 12, No. 1 (1984), as well as visual comparisons of sequence data, and a distance matrix is generated to reflect evolutionary distances between the aligned sequences in order to identify distinct members. This alignment is used to precisely identify conserved motifs that may be used for PCR amplification. In a preferred embodiment, in identifying oligonucleotide sequences, more weight is placed on conservation of the three to four 3' codons for each of the primers than for the 5' end of the sequence.

In one example, the conserved regions of known PTKs was compared. Publicly available PTKs and their sources (Accession Nos.) are set forth below at Table 1:

TABLE 1

Examples Of Publicly Available PTKs And Their Source

| Number | PTK | ACC No. | Number | PTK | ACC No. |
|---|---|---|---|---|---|
| 1 | EGFR | X00588 | 48 | DDR | L11315 |
| 2 | HER2 | M11730 | 49 | TYRO10 | S42621 |
| 3 | HER3 | M34309 | 50 | ROS | M34353 |
| 4 | HER4 | L07868 | 51 | RET | X15262 |
| 5 | INSR | M10051 | 52 | LTK | D16105 |
| 6 | IGF1R | X04434 | 53 | ROR1 | M97675 |
| 7 | IRR | J05046 | 54 | ROR2 | M97639 |
| 8 | PDGFRa | M22734 | 55 | TORPEDO | L11311 |
| 9 | PDGFRb | J03278 | 56 | XMRK | X16891 |
| 10 | CSF1R | X03663 | 57 | TORSO | X15150 |
| 11 | KIT | X06182 | 58 | SRC | 17031 |
| 12 | FLK2 | U02687 | 59 | YES | M15990 |
| 13 | FLT1 | X51602 | 60 | FYN | M14676 |
| 14 | FLK1 | S53103 | 61 | LYN | M16038 |
| 15 | FLT4 | X68203 | 62 | LCK | X13529 |
| 16 | FGFR1 | X51803 | 63 | BLK | M30903 |
| 17 | FGFR2 | X52832 | 64 | HCK | M16591 |
| 18 | FGFR3 | M58051 | 65 | FGR | M19722 |
| 19 | FGFR4 | X57205 | 66 | YRK | X67786 |
| 21 | MET | X54559 | 67 | BRK | X78549 |
| 22 | SFA | L12024 | 68 | MKK3 | HS8034 |
| 23 | RON | X70040 | 69 | BTK | X58957 |
| 24 | TRKA | M23102 | 70 | TEC | X55663 |
| 25 | TRKB | X17647 | 71 | LYK | D13720 |
| 26 | TRKC | L03813 | 73 | CSK | X60114 |
| 27 | AXL | M76125 | 74 | MKK1 | L18974 |
| 28 | TYRO3 | D17517 | 75 | TXK | L27071 |
| 29 | MER | U08023 | 76 | ABL | X16416 |
| 30 | TIE | X60957 | 77 | ARG | M35296 |
| 31 | TEK | L06139 | 78 | ZAP70 | L05148 |
| 32 | EPH | M18391 | 79 | SYK | L28824 |
| 33 | ECK | M59371 | 80 | FPS/FES | M14209 |
| 34 | EEK | X59290 | 81 | FER | J03358 |
| 35 | ERK | D31661 | 82 | JAK1 | L24895 |
| 36 | ELK | M59814 | 83 | JAK2 | L16956 |
| 37 | EHK1 | S68024 | 84 | TYK2 | X54637 |
| 38 | EHK2 | S68030 | 85 | JAK3 | U09607 |
| 39 | SEK | S57168 | 86 | FAK | L13616 |
| 40 | HEK | M83941 | 88 | ACK | L13738 |
| 41 | HEK2 | S65702 | 89 | LIMK | D26309 |
| 42 | MYK1 | U06834 | 91 | ALK | U04946 |
| 43 | CEK9 | Z19060 | 92 | STK | X74736 |
| 46 | MDK1 | X79082 | 93 | SRM | D26186 |
| 47 | RYK | X69970 | | | |

In a second example, the conserved regions of known PTPs were compared. Publicly available PTPs and their sources (Accession Nos.) are set forth below at Table 2:

TABLE 2

Examples Of Publicly Available PTPKs And Their Source

| Number | PTP | ACC No. | Number | PTP | ACC No. |
|---|---|---|---|---|---|
| 1 | PTP-a | M34668 | 26 | PTP-H1 | M64572 |
| 2 | PTPa[1] | M34668 | 27 | PTP-BAS1 | D21209 |
| 3 | PTP-e | X54134 | 28 | PTP-D1 | X75910 |
| 5 | PTP-g | L09247 | 29 | PTP36 | D31842 |
| 6 | PTP-s | L19181 | 30 | PTP-1B | M31724 |
| 7 | PTP-z | M93426 | 31 | TC-PTP | M25393 |
| 8 | PTP-b | X54131 | 32 | PTP-STEP | S49400 |
| 9 | DEP-1 | U10886 | 33 | LC-PTP | D11327 |
| 11 | GLEPP1 | U09490 | 34 | PTP-SL | U14914 |
| 12 | GLEPP1-h | U20489 | 35 | SuPTP03[2] | |
| 13 | PTP-SAP | D15049 | 36 | PTP-PEST | M93425 |
| 14 | PTP-ESP | U36488 | 37 | ZPEP | M90388 |
| 15 | PTP-d | X54133 | 38 | 1A-2/PTP | L18983 |
| 16 | LAR | Y00815 | 40 | PTP20 | U69673 |
| 17 | LAR[1] | Y00815 | 41 | PTP-CL100 | X68277 |
| 18 | PTP-OST | L36884 | 42 | PTP-k | L10106 |
| 19 | PTP-$\mu$ | X58288 | 43 | PTP-CIP2 | L25876 |
| 20 | CD45 | Y00638 | 44 | KKP2 | Z30313 |
| 21 | PTP-$\lambda$ | L13285 | 45 | PTP-PAC1 | L11329 |
| 22 | PTP-MEG2 | M83738 | 47 | CRYP | L32780 |
| 23 | PTP-1C | X62055 | 48 | VH3 | U16996 |
| 24 | PTP-1D | X70766 | 49 | M0T12 | Y08569 AF007555, Q92932 |
| 25 | PTP-MEG | M68941 | | | — |

[1]C-terminal PTP domain
[2]A presumed novel PTP related to LC-PTP cloned at SUGEN now believed to be murine LC-PTP.

The conserved regions of interest were then aligned and a consensus degenerate sequence derived. As illustration, assuming FGFR1, FGFR2, FGFR3, CCK4 and MET represented all of the known PTKS, following alignment, the partial sequences corresponding to one of the conserved regions would be:

| | | | | | | |
|---|---|---|---|---|---|---|
| FGFR1 | ...W | M | A | P | E | A | (SEQ ID NO: 1)... |
| FGFR2 | ...W | M | A | P | E | A | (SEQ ID NO: 1)... |
| FGFR3 | ...W | M | A | P | E | A | (SEQ ID NO: 1)... |
| CCK4 | ...W | M | S | P | E | A | (SEQ ID NO: 2)... |
| MET | ...W | M | A | L | E | S | (SEQ ID NO: 3)... |

The representative consensus sequence (sequence comprised of the amino acids having the highest frequency at each position) for this region would be: . . . W M A P E A . . .

and could be used as a degenerate oligonucleotide primer. Comparing the sequences for these PTKs and PTPs, the following degenerate oligonucleotide sequences for PTKs and PTPs were identified:

PTK Forward Primers

1. For PTK transcript imaging (all PTKs except the src subfamily):

| Oligo Name | Sequence (IUPAC code) | |
|---|---|---|
| HRDRTK | 5'- CCGGGATCCACAAGCTTCCCTNCAYMRDGAYNTNGC-3' | (SEQ ID NO: 4) |
| HRDH3a | 5'- CCGGGATCCACAAGCTTCCGTNCAYMGNAAYYTNGC-3' | (SEQ ID NO: 5) |
| HRDIAFAK | 5'- CCGGGATCCACAAGCTTCCCTNCAYMRDGAYATHGC-3' | (SEQ ID NO: 6) |

These sequences correspond to the 5' end of the selected motif and represent three distinct variations of this motif.

2. For PTK "src" transcript imaging:

| Oligo Name | Sequence (IUPAC code) | |
|---|---|---|
| HRDSRC3 | 5'-CCGGGATCCACAAGCTTCCRTNCAYMGNGAYYTNMG-3' | (SEQ ID NO: 7) |
| HRDA3 | 5'-CCGGGATCCACAAGCTTCCCTNCAYMRDGAYNTNAA-3' | (SEQ ID NO: 8) |

These sequences correspond to the 5' end of the selected motif and represent two (2) subclasses of known tyrosine kinases that are not covered by the three (3) main forward primers.

PTK Reverse Primers

3. For PTK and transcript imaging (all PTKs except the src and LIMK subfamily):

| Oligo Name | Sequence (IUPAC Code) | |
|---|---|---|
| DVWSRTK | 5'-CCGAATTCACAAGATCTCCCAYNCCRWANSWCCANACRTC-3' | (SEQ ID NO: 9) |
| DSWLTKb | 5'-CCGAATTCACAAGATCTCCDATNCCRAANSWCCANSWRTC-3' | (SEQ ID NO: 10) |
| DAWST11 | 5'-CCGAATTCACAAGATCTCCNACNCCRTANSWCCANGCRTC-3' | (SEQ ID NO: 11) |
| DIWSRTK | 5'-CCGAATTCACAAGATCTCCCAYNCCRWANSWCCADATRTC-3' | (SEQ ID NO: 12) |
| DVWAFAK | 5'-CCGAATTCACAAGATCTCCNACNCCRAANGCCCANACRTC 3' | (SEQ ID NO: 13) |
| DTWMPYK1 | 5'-CCGAATTCACAAGATCTCCNACNCCRAANGCCCANGTRTC 3' | (SEQ ID NO: 14) |

These sequences correspond to the 3' end of the selected motif.

4. For tyrosine kinase "src" transcript imaging:

| Oligo Name | Sequence (IUPAC Code) | |
|---|---|---|
| DVWSRTK | 5'-CCGAATTCACAAGATCTCCCAYNCCRWANSWCCANACRTC-3' | (SEQ ID NO: 15) |
| DIFSA3 | 5'-CCGAATTCACAAGATCTCCCAYNCCRWANSWRAANACRTC-3' | (SEQ ID NO: 16) |

The PTK oligonucleotides preferentially contain a nineteen (19) base pair "tag" on their 5' end to allow for higher annealing temperatures following the initial low stringency PCR cycles.

5. Although not used in the preferred embodiment of this invention, the following sequences may also be used:

| Oligo Name | Sequence (IUPAC code) |
|---|---|
| TRKB | CCGAATTCACAAGATCTCCNACNCCNARNSWCCANACRTC (SEQ ID NO: 19) |
| DIWA | CCGAATTCACAAGATCTCCCAYNCCRWANGCCCADATRTC (SEQ ID NO: 20) |
| DVWIR | CCGAATTCACAAGATCTCCNACNCCRAANSWCCACATRTC (SEQ ID NO:21) |

PTP Forward Primer

6. For PTP transcript imaging:

| Oligo Name | Sequence (IUPAC code) | |
|---|---|---|
| PTPDWF | 5'-GAYTTYTGGVRNATGRTNTGGGA-3' | (SEQ ID NO: 17) |

PTP Reverse Primer

7. For PTP transcript imaging:

| Oligo Name | Sequence (IUPAC code) | |
|---|---|---|
| PTPHCSA- | 5'-CGGCCSAYNCCNGCNSWRCARTG- 3' | (SEQ ID NO: 18) |

These forward and reverse sequences correspond to the selected motif and represent all of the known tyrosine phosphatases. See also, FIGS. 1A, 1B and 1C.

In another example, the positions of total degeneracy, "N", (A, T, G, or C) of the above oligonucleotide sequences were replaced by inosine ("I"), which base pairs to all four nucleotides with similar affinity.

The oligonucleotides of the present invention may be synthesized by any known technique, including automated synthesis. Information on how to synthesize and purify conventional oligonucleotides can be found, among other places, in Eckstein, *Oligonucleotide And Analogues: A Practical Approach,* 1992, Oxford University Press.

For example, the oligonucleotides may be synthesized using commercially available synthesizers, including the Applied Biosystems 394 DNA Synthesizer or a Cyclone Plus DNA Synthesizer (Millipore), using established phosphoramidite chemistry.

The oligonucleotides are removed from the column using known techniques. For example, the oligonucleotides may be removed from the column with 37% ammonium and the protecting groups are removed by incubation at 55° C. for two (2) hours. The oligonucleotides are then dried in a Speedvac™, dissolved in 100 µl water and then precipitated with three volumes ethanol/0.3M sodium acetate. The pellet is then dissolved in 70% ethanol and 100 µL TE buffer. These oligonucleotides may be used without further purification.

The primer degeneracy for the biomolecules may vary from multiple hundred to multiple thousand-fold. For example, the primer degeneracy for PTK targets varied, in one embodiment, from 1024-fold to 3072-fold. In a second embodiment, the primers for PTPs had degeneracies of 768-fold to 4096-fold.

Preferentially, the oligonucleotides should not be purified using an oligonucleotide purification column.

After the appropriate primer sets have been determined and synthesized, the appropriate ratio and combination of each primer to permit equal amplification of all known members of a biomolecule family was determined by an initial rational determination followed by an iterative process wherein, for example, the primers are first pooled in various ratios corresponding to the frequency in which the specific targeted motif appear. Iterative changes are thereafter made until a final pool capable of amplifying each plasmid with similar efficiency is determined.

In a preferred embodiment, the ratio of oligonucleotide primers described above used for the detection and relative abundance of all known PTK subfamilies except "src" ("transcript imaging") is:

| Oligo Name | Oligo Ratio |
| --- | --- |
| HRDRTK | 7 |
| HRDH3a | 6 |
| HRDIAFAK | 2 |
| DVWSRTK | 10 |
| DSWLTKb | 1 |
| DAWST11 | 1 |
| DIWSRTK | 1 |
| DVWAFAK | 1 |
| DTWMPYK1 | 1 |

In a preferred embodiment, the ratio of oligonucleotide primers, described above, used for PTK "src" transcript imaging is:

| Oligo Name | Oligo Ratio |
| --- | --- |
| HRDSRC3 | 7 |
| HRDA3 | 13 |
| DVWSRTK | 10 |
| DIFSA3 | 10 |

In a preferred embodiment, the ratio of oligonucleotide primers, described above, used for PTP transcript imaging is:

| Oligo Name | Oligo Ratio |
| --- | --- |
| PTPDFW | 1 |
| PTPHCSA- | 1 |

The total concentration of oligonucleotide primers used should be sufficient to permit the expression of a representative sample of all known members of the biomolecule family. For PTKs, PTPs and serine/threonine kinases, this concentration is preferentially between 2–10 $\mu$M final.

PCR Amplification

The RNA or single-stranded cDNA template may be extracted from the biological sample using known techniques which can be found, among other places, in Sambrook et al., *Molecular Cloning: A Laboratory Manual* (Second Edition), 1989, Cold Spring Harbor Laboratory Press, and Berger and Kimmel (Eds.), *Methods in Enzymology* (Vol. 152): *Guide to Molecular Cloning Techniques*, 1987, Academic Press, Inc. Additionally, commercially available kits may be used to isolate the RNA from the sample, and preferably the RNA isolation kit of InVitrogen. Selection of an appropriate RNA isolation protocol will depend, among other factors, upon the amount and source of the biological sample.

More specifically, when sample size is not limiting, total RNA can be isolated from mammalian cell lines or tissue samples using the Guanidine Salts/Phenol extraction protocol of Chomczynski and Sacchi. Chomczynski and Sacchi, 1987, *Anal. Biochem* 162:156. To the extent that there is only limited sample size available, as in the case for example with neuronal cells, FACS sorted hematopoietic cells, or tumor tissue thin sections, the Invitrogen™ Microfast Track protocol may be used. Such method may be used for samples comprised of as few as 1000 cells where the frozen cell pellet or tissue properly prepared, such as when such pellet or tissue sample is resuspended in lysis buffer, incubated with oligo(dT) cellulose and poly(A) RNA is purified by applying the mixture to a spin column.

First strand cDNA may be prepared from the RNA templates by known and/or commercially available techniques. For example, first strand cDNA may be synthesized from an RNA template using the SuperScript Preamplification System (GIBCO BRL) following the manufacturer's protocol wherein the reaction used 10 $\mu$g total RNA or 2 $\mu$g poly(A)$^{+RNA\ with}$ 1.5 $\mu$g oligo(dT)$_{12-18}$ in a reaction volume of 20 $\mu$l. The resulting product is treated with RNaseH and diluted to 100 $\mu$l with H$_2$O.

Alternatively, the RNA precipitated from the Invitrogen™ Microfast Track protocol can be resuspended in H$_2$O and first strand synthesis performed with 0.5 $\mu$g oligo(dT)$_{12-18}$ in a final reaction volume of 20 $\mu$l.

For subsequent PCR amplification, about 1–4 $\mu$l of these single stranded DNAs were used in each reaction.

The amount of RNA or single stranded cDNA used as a template in PCR may be about 40–200 ng. For purposes of conducting controls, as described below, approximately 1–20 ng of plasmid DNA may be used as a template.

For purposes of this invention, appropriate conditions for PCR comprise a multiple step process in which the reaction is first conducted at low stringency conditions (e.g. low annealing temperature) to permit amplification of the available kinases. The reaction conditions are then changed to reflect more stringent conditions (e.g. high annealing temperature) to permit specific amplification. The preparation of the abundant amounts of template by incubation at low stringency conditions (the "ramping step") plays an important role in transcript imaging. For PTKs, PTPs and/or serine/threonine kinases, the selected pools of degenerate primers were then prepared for the PCR. In one embodiment, the selected pools are added at a final concentration of 5 $\mu$M to a mixture containing 10 mM Tris HCl (pH 8.3), 50 mM KCL, 1.5 mM MgCl$_2$, 200 $\mu$M each of deoxynucleoside triphosphate, 0.001% gelatin and 1.5 U AmpliTaq DNA Polymerase (Perkin-Elmer/Cetus) and 1–4 $\mu$l cDNA. The preferred parameters for conducting PCR for tyrosine kinases are:

Step 1: Incubation at 95° C. for three (3) minutes;

Step 2: Incubation at 94° C. for thirty (30) seconds;

Step 3: Incubation at 37° C. for one (1) minute (permitting low stringency annealing);

Step 4: Ramp to 72° C. over two (2) minutes;

Step 5: Incubation at 72° C. for one (1) minute;

Step 6: Repeat Steps 2–5 two additional times such that Steps 2–5 are performed a total of three (3) times.

Step 7: Incubation at 94° C. for thirty (30) seconds;

Step 8: Incubation at 50° C. for one (1) minute (high stringency annealing);

Step 9: Incubation at 72° C. for one (1) minute;

Step 10: Repeat Steps 7–9 thirty-four (34) additional times such that the Steps 7–9 are performed a total of thirty-five (35) times. The resulting "amplification products" are then analyzed by agarose gel electrophoresis and visualization with ethidium bromide staining.

Labelling And Slot Blot Assay

The PCR amplification products from the primary amplification may be confirmed by agarose gel electrophoresis and purified using known and/or commercially available techniques, such as QIAquick PCR purification columns (Quiagen), to remove excess primers, primer dimers and free dNTPs. Column purification is preferred so as to avoid cross-contamination of samples, which is problematic with gel electrophoresis.

A portion of the purified DNA is then reamplified using a PCR protocol identical to that described above, except that the dCTP concentration was reduced about 33-fold with the inclusion of $^{33}$P-dCTP. The $^{33}$P-labeled products should then be NH$_4$OAc/EtOH precipitated, quantified and heat denatured prior to hybridization using the following slot blot protocol.

The biomolecule expression level may then be determined and quantified using known blotting and hybridization techniques, including dot blot- or slot blot-filter hybridization. Such techniques are described in, among other places, Sambrook, et al., supra and Burger and Kimmel, supra.

As a prerequisite to determining expression levels using dot blot- or slot blot-filter hybridization, one must first identify and obtain cDNA clones for each member of a biomolecule family. To the extent that such clones are not publicly available, the corresponding cDNAs, or alternatively, the relevant domains, may be obtained using methods known in the art. See e.g.,, Sambrook, et al., supra and Burger and Kimmel, supra. For example, the cytoplasmic or catalytic domains of PTK, may be isolated by use of PCR with oligonucleotide primers on single strand cDNA from a source known to contain the transcript. The specific clones were then inserted into vectors such as pBS/SKII+ (Stratagene), PCRII, RK5 and cDM8. Maxi-prep plasmid DNA may be purified by Wizard (Promega) or Quiagen methods. Each plasmid should then be verified by restriction digests and DNA sequencing and concentrations determined, for example, on a UV spectrophotometer.

Molar ratios of each plasmid should then be calculated to ensure that equimolar amounts of each plasmid are applied to the slot blot hybridization filter. Preferentially, molar ratios are calculated by taking the size (in base pairs) of the region spanned by the primers (about 210 base pairs for kinases and 320 base pairs for phosphatases) divided by the total size (in base pairs) of the plasmid. About 0.3–5.0 µg of each DNA is applied to each slot on nylon membranes using a 48-slot apparatus. The DNA is then denatured, neutralized and fixed by UV-cross-linking.

In one embodiment, PTK, PTP or serine/threonine kinase expression have been determined and quantified using slot blot analysis according to the method of Kafatos et al., 1979, *Nucleic Acids Res.* 7:1541.

In a second embodiment, hybridization is run at appropriate conditions to all equal detection of murine and human clones for the same PTK, PTP or serine/threonine kinase, while preventing cross-reactivity between related members. For example, the hybridization may be conducted at 42° C. overnight in 50% formamide/5× SSC/0.025M NaHPO$_4$/1× Denhardt's/20µg/ml Salmon Sperm DNA. The filters are then washed in 1× SSC at 65° C. and exposed on the phosphorimager (Molecular Dynamics).

Results may be presented as the percent of total counts above background for all DNAs hybridized to allow for a determination of the relative abundance of each biomolecule, such as kinase or phosphatase, in a given sample.

Controls For Oligonucleotide Pool

To determine whether an appropriate pool of oligonucleotides had been selected, controls for specificity may be conducted. Specifically, the following measures were taken to ensure the veracity and accuracy of the instant assay and methods:

Control 1: Conduct PCR with the final pool of oligonucleotides against a sufficient amount, and preferentially 10 ng, of each individual plasmid and analyze the products by agarose gel electrophoresis, preferably 2% agarose gels stained, where the DNA is stained with ethidium bromide and photographed on a UV light box, to confirm that the pool can detect each DNA sequence with similar efficiency. FIG. 2 sets forth the results from this control for PTK samples;

Control 2: Generate a radiolabeled probe by applying the degenerate oligos in a PCR reaction against an equimolar pool of all known kinases and/or phosphatases. This radiolabeled PCR product is then used to probe a blot containing an equimolar amount of all DNAs. Optimally, every DNA has a similar intensity of hybridizing band, as evidenced at FIGS. 3a and 3B for PTPs and PTKs, respectively;

Control 3: Hybridize blots containing rat and human homologues with probes generated from the same or different species template to support the application of this protocol to templates from diverse species; and Control 4: Compare analysis results with results from multiple Northern blot analyses of same sample to verify that the RNA expression levels determined by transcript imaging correlate with the actual amount of specific RNA that is present in the sample.

For purposes of this invention, any one or combination of the above-described controls or other known controls may be used.

5.2. Application Of The Claimed Methods

The assay and method of the present invention may be used in any diagnostic, therapeutic or research application where determination and quantification of a biomolecule's relative expression level are important.

Diagnostic applications may include, for example, the determination of a given pathological tissue's (e.g. cancer) expression profile for a known set of biomolecules, such as tyrosine kinases or tyrosine phosphatases. Abnormal transcript amounts of such biomolecules may be elucidated and certain subsets of a given disease, such as HER2 driven cancer, identified. Other diagnostic uses may include the comparison of the transcription levels of such biomolecules before and after treatment with agents that induce cell growth and differentiation, cell cycle arrest, or apoptosis. The present invention also may be used for the analysis of more complex samples such as hippocampal tissue following an excitatory stimulus or a toxic insult, or tumor tissue before and after radiation or chemotherapy to determine if there is a significant change in the expression of specific transcripts. Such findings could have implications for continuing or modifying subsequent therapy.

Therapeutically, the assays and methods of the present invention enable the implementation of targeted drug therapy where a drug is rationally selected from a panel of specific inhibitors based on the tumors expression profile. For example, in cases of diagnosed HER2 driven cancer, HER2 specific inhibitors may be employed as therapeutic compounds. Fry, 1994, *Exp. Opin. Invest. Drugs* 3(6) :577–595. The efficacy of the compound may be tested and verified on cultured cells of the given tumor sample prior to in vivo application. Following identification of a transcript gene that is specifically overexpressed, one can further corroborate these findings at the protein level by immunohistochemical staining using specific monoclonal antibodies. The present invention may also have therapeutic applications in the treatment of metastasized cells following tumor excision. As set forth in Hynes and Stern, 1994, *Biochim. Biophys. Acta* 1198:165–184, the biomolecule expression profile of tumor and metastatic cells within one patient is similar, if not identical. Thus, the present invention may be used to identify a treatment regimen to prevent the proliferation of metastatic cells by determining the abnormal expression profile of a specific tumor cell(s) and rendering treatment directed to such expression. The present invention may further be used to monitor disease progress and the efficacy of treatment, especially in metabolic disease states.

Research applications may include the imaging of samples to identify cell lines whose profile is most similar to a specific primary cell or diseased cell population, which can be used as experimental disease model. Further research applications include the identification of known or unknown molecules associated with the development of certain pathological disorders.

6. EXAMPLE

Using the methods, protocols and techniques described above, a biological sample was tested to determine the known PTPs expression levels in an sample. Specifically:

6.1. Transcript Imaging "Pool" Control For Determining PTP Expression Levels The methods described above were used to develop a panel for use in determining the expression level of PTPs in a sample. To validate this panel, a control experiment was performed according to the controls described at Section 5.1. The results of the control pool experiment for PTP transcript imaging is set forth at FIG. 3A. The identity of each known member of the PTPs family of biomolecules (slot number/PTP) for which expression level was determined is set forth at Table 2.

6.2. Transcript Imaging To Determine PTKs Expression Levels

The methods described above were used to determine the PTKs expression level of two human breast tumor cell lines (SKBR3 and BT474), a human epidermoid carcinoma cell line (A431) and one normal breast epithelial cell line (HBL100). The results of the transcript imaging of each of these cells are set forth at FIGS. 4A and 4B. The control used to validate the PTKs transcript imaging is set forth at FIG. 39. The identity of each known member of the PTKs family of biomolecules (slot number/PTK) for which expression level was determined is set forth at Table 3.

The amount of each PTK expressed by the various tested cells was quantitated as described above. The results of this quantification, as it corresponds to the transcript imaging set forth at FIGS. 4A and 4B are:

TABLE 3

| No. | PTK | HBL100 Sig. | % | A431 Sig. | % | SKBR3 Sig. | % | BT474 Sig. | % |
|---|---|---|---|---|---|---|---|---|---|
| 1 | EGFR | 65667 | 2.2 | 29747718 | 21.6 | 2342574 | 12.4 | 266074 | 3.0 |
| 2 | HER2 | 9759 | 0.3 | 88633 | 0.6 | 3566659 | 18.9 | 774511 | 8.7 |
| 3 | HER3 | 1605 | 0.1 | 70590 | 0.5 | 299157 | 1.6 | 105816 | 1.2 |
| 4 | HER4 | 3281 | 0.1 | 11346 | 0.1 | 34249 | 0.2 | 15233 | 0.2 |
| 5 | INSR | 8643 | 0.3 | 24042 | 0.2 | 130324 | 0.7 | 49704 | 0.6 |
| 6 | IGF 1R | 18315 | 0.6 | 233445 | 1.7 | 123107 | 0.7 | 147688 | 1.7 |
| 7 | IRR | 6795 | 0.2 | 139648 | 1.0 | 130078 | 0.7 | 114954 | 1.3 |
| 8 | PDGF Ra | 5493 | 0.2 | 4828 | 0.0 | 71304 | 0.4 | 18680 | 0.2 |
| 9 | PDGF Rb | 5780 | 0.2 | 3299 | 0.0 | 15719 | 0.1 | 6332 | 0.1 |
| 10 | CSF 1R | 21478 | 0.7 | 16816 | 0.1 | 557036 | 3.0 | 66507 | 0.7 |
| 11 | KIT | 8049 | 0.3 | 2609 | 0.0 | 15802 | 0.1 | 13786 | 0.2 |
| 12 | FLK2 | 24295 | 0.8 | 3973 | 0.0 | 40240 | 0.2 | 46366 | 0.5 |
| 13 | FLT1 | 2996 | 0.1 | 11820 | 0.1 | 11518 | 0.1 | 16260 | 0.2 |
| 14 | FLK1 | 4168 | 0.1 | 11886 | 0.1 | 23305 | 0.1 | 18646 | 0.2 |
| 15 | FLT4 | 8102 | 0.3 | 8140 | 0.1 | 70806 | 0.4 | 31183 | 0.4 |
| 16 | FGFR1 | 281304 | 9.2 | 45523 | 3.3 | 1226251 | 6.5 | 917262 | 10.3 |
| 17 | FGFR2 | 54641 | 1.8 | 804018 | 5.8 | 1466652 | 7.8 | 37300 | 0.4 |
| 20 | CCK4 | 13911 | 0.5 | 50241 | 0.4 | 25562 | 0.1 | 6257 | 0.1 |
| 21 | MET | 7557 | 0.2 | 36639 | 0.3 | 43861 | 0.2 | 38523 | 0.4 |
| 23 | RON | 2973 | 0.3 | 33809 | 0.2 | 68528 | 0.4 | 20016 | 0.2 |
| 24 | TRKA | 4005 | 0.1 | 24774 | 0.2 | 45754 | 0.2 | 25506 | 0.3 |
| 25 | TRKE | 9229 | 0.3 | 22444 | 0.2 | 80969 | 0.4 | 34905 | 0.4 |
| 26 | TRKC | 8187 | 0.3 | 93321 | 0.7 | 173290 | 0.9 | 38662 | 0.4 |
| 27 | AXL | 124753 | 4.1 | 175374 | 1.3 | 67951 | 0.4 | 9831 | 0.1 |
| 28 | TYR O3 | 260245 | 8.5 | 302189 | 2.2 | 268226 | 1.4 | 1053118 | 11.9 |
| 29 | MER | 3929 | 0.1 | 32469 | 0.2 | 46516 | 0.2 | 69401 | 0.8 |
| 30 | TIE | 3594 | 0.1 | 21266 | 0.2 | 27687 | 0.1 | 16465 | 0.2 |
| 33 | TEK | 3319 | 0.1 | 10066 | 0.1 | 16199 | 0.1 | 7564 | 0.1 |
| 32 | EPH | 4224 | 0.1 | 548112 | 4.0 | 963285 | 5.1 | 141838 | 1.6 |
| 33 | ECH | 13908 | 0.5 | 47718 | 0.3 | 62342 | 0.3 | 9320 | 0.1 |
| 34 | EEK | 14764 | 0.5 | 24917 | 0.2 | 59253 | 0.3 | 15455 | 0.2 |
| 35 | ERK | 19907 | 0.7 | 430147 | 3.1 | 495017 | 2.6 | 126618 | 1.4 |
| 36 | ELK | 4632 | 0.2 | 14665 | 0.1 | 46726 | 0.2 | 11578 | 0.1 |
| 37 | EHK3 | 5441 | 0.2 | 21687 | 0.2 | 38762 | 0.2 | 10944 | 0.1 |
| 38 | EHK2 | 11683 | 0.4 | 28208 | 0.2 | 24339 | 0.1 | 8684 | 0.1 |
| 39 | SEK | 20443 | 0.7 | 165258 | 1.2 | 155831 | 0.8 | 35997 | 0.4 |
| 40 | HKK | 7533 | 0.2 | 16097 | 0.1 | 10030 | 0.1 | 5159 | 0.1 |
| 41 | HEK2 | 33578 | 1.1 | 151577 | 1.1 | 227528 | 1.2 | 103213 | 1.2 |
| 42 | MYK1 | 41988 | 1.4 | 70019 | 0.5 | 284032 | 1.5 | 129907 | 1.5 |

TABLE 3-continued

| | | HBL100 | | A431 | | SKBR3 | | BT474 | |
|---|---|---|---|---|---|---|---|---|---|
| No. | PTK | Sig. | % | Sig. | % | Sig. | % | Sig. | % |
| 43 | CEK9 | 4030 | 0.1 | 10187 | 0.1 | 16218 | 0.1 | 7444 | 0.1 |
| 45 | HTK | 13257 | 0.4 | 32423 | 0.2 | 133294 | 0.7 | 45424 | 0.5 |
| 46 | MDK3 | 77287 | 2.5 | 223106 | 1.6 | 255829 | 1.4 | 77070 | 0.9 |
| 47 | RYK | 88540 | 2.9 | 67797 | 0.5 | 312634 | 1.7 | 79053 | 0.9 |
| 48 | DDR | 541555 | 17.7 | 2608493 | 18.9 | 856303 | 4.5 | 1116874 | 12.6 |
| 49 | TYR 010 | 241994 | 7.9 | 485699 | 3.5 | 615840 | 3.3 | 149065 | 1.7 |
| 50 | ROS | 11873 | 0.4 | 17266 | 0.1 | 30205 | 0.2 | 15907 | 0.2 |
| 51 | RET | 5680 | 0.2 | 3973 | 0.0 | 15517 | 0.1 | 47340 | 0.5 |
| 52 | LTK | 4448 | 0.1 | 2740 | 0.0 | 5827 | 0.0 | 1114 | 0.0 |
| 53 | ROR1 | 5202 | 0.1 | 55359 | 0.4 | 5529 | 0.0 | 10079 | 0.1 |
| 54 | ROR2 | 7062 | 0.2 | 18660 | 0.1 | 13066 | 0.1 | 27785 | 0.3 |
| 67 | BRK | 18089 | 0.6 | 543774 | 3.9 | 124283 | 0.7 | 801266 | 9.0 |
| 68 | MKK3 | 53449 | 1.8 | 82779 | 0.6 | 214531 | 1.1 | 201933 | 2.3 |
| 69 | BTK | 6162 | 0.2 | 13398 | 0.1 | 10898 | 0.1 | 10631 | 0.1 |
| 70 | TEC | 39500 | 1.3 | 10234 | 0.1 | 8245 | 0.0 | 38712 | 0.4 |
| 73 | LYK | 3903 | 0.1 | 17369 | 0.1 | 16106 | 0.1 | 5463 | 0.1 |
| 72 | MKK2 | 6676 | 0.2 | 14420 | 0.1 | 24349 | 0.1 | 22179 | 0.2 |
| 73 | CSK | 9212 | 0.3 | 140977 | 1.0 | 97535 | 0.5 | 110591 | 1.2 |
| 74 | MKK1 | 7793 | 0.3 | 39842 | 0.3 | 67901 | 0.4 | 50429 | 0.6 |
| 76 | ABL | 10862 | 0.4 | 50631 | 0.4 | 53537 | 0.3 | 134507 | 1.5 |
| 77 | ARG | 181860 | 6.0 | 179402 | 1.3 | 71233 | 0.4 | 111533 | 1.3 |
| 78 | ZAP 70 | 3389 | 0.1 | 15030 | 0.1 | 2867 | 0.0 | 5640 | 0.1 |
| 79 | SYK | 2411 | 0.1 | 25330 | 0.2 | 18356 | 0.1 | 10188 | 0.1 |
| 80 | FPS/FES | 2865 | 0.1 | 16542 | 0.1 | 21831 | 0.1 | 14247 | 0.2 |
| 81 | FEK | 73482 | 2.4 | 284481 | 2.1 | 448653 | 2.4 | 159957 | 1.8 |
| 82 | JAK1 | 289045 | 9.5 | 646246 | 4.7 | 1145255 | 6.1 | 513072 | 5.8 |
| 833 | JAK2 | 60766 | 2.0 | 297019 | 2.2 | 223705 | 1.2 | 111837 | 1.3 |
| 84 | TYK2 | 8100 | 0.3 | 18343 | 0.1 | 25674 | 0.1 | 14262 | 0.2 |
| 85 | JAK3 | 32473 | 1.1 | 35754 | 0.3 | 86234 | 0.5 | 13621 | 0.1 |
| 86 | FAK | 78174 | 2.6 | 573957 | 4.2 | 492724 | 2.6 | 38223 | 4.3 |
| 87 | PYK2 | 8665 | 0.3 | 46804 | 0.3 | 33326 | 0.2 | 24170 | 0.3 |
| 88 | ACK | 4473 | 0.1 | 11237 | 0.1 | 12597 | 0.1 | 9365 | 0.1 |
| | TOTAL | 3052251 | | 13775657 | | 18832131 | | 8886244 | |

6.3. Additional Control Experiment

In addition to the controls set forth at FIG. 3A (PTPs) and 3B (PTKs), an additional control was used to validate the findings set forth at Section 5.1. This control experiment was conducted according to the method described as "Control 1," described above. Specifically, PCR was conducted with the final pool of oligonucleotides against 10 ng of each individual plasmid and the PCR products were analyzed by agarose gel electrophoresis, preferably 2% agarose gels stained with ethidium bromide and photographed on a UV light box. The results of such control experiment are set forth at FIGS. 4A and 4B and demonstrate an unbiased representation of a subset of PTKs in the pool of amplification products.

The present invention is not to be limited in scope by the exemplified embodiments which are intended as illustrations of single aspects of the invention, and methods which are functionally equivalent are within the scope of the invention. Indeed, various modifications of the invention in addition to those described herein will become apparent to those skilled in the art from the foregoing description and accompanying figures. Such modifications are intended to fall within the scope of the appended claims.

All references cited within the body of the instant specification are hereby incorporated by reference in their entirety.

What is claimed:

1. A method for simultaneously detecting and quantifying the expression of a panel of tyrosine kinases from a biological sample of any vertebrate species comprising the steps of:
(a) providing a representative pool of oligonucleotides having a sequence which hybridizes to conserved regions in the mRNA or cDNA of said panel of tyrosine kinases, which pool has been tested and determined to provide for the amplification of nucleic acids encoding said panel of tyrosine kinases with essentially the same efficiency;
(b) amplifying said mRNA or cDNA of the biological sample using said pool of oligonucleotides provided in step (a) so that an amplified composition is generated, wherein amplification of nucleic acids encoding said panel of tyrosine kinases reflects their relative expression level within the biological sample; and (c) assaying the amplified composition for the presence of nucleic acids encoding said panel of tyrosine kinases.

2. The method of claim 1 wherein the mRNA or cDNA of the biological sample is extracted and isolated from the biological sample prior to amplification.

3. The method of claim 1 wherein the assay method of step (c) is selected from the group consisting of dot analysis, slot analysis, Northern analysis and filter hybridization.

4. A method for simultaneously detecting and quantifying the expression of a panel of tyrosine kinases from a biological sample of any vertebrate species comprising the steps of:

(a) providing a representative pool of oligonucleotides having a sequence which hybridizes to conserved regions in the mRNA or cDNA of said panel of tyrosine kinases, which pool has been tested and determined to provide for the amplification of nucleic acids encoding said panel of tyrosine kinases with essentially the same efficiency, wherein said representative pool of oligonucleotides is comprised of at least two oligonucleotides selected from the group consisting of:
CCGGGATCCACAAGCTTCCCTNCAYMRD-GAYNTNGC (SEQ ID NO:4),
CCGGGATCCACAAGCTTCCGTNCAYMG-NAAYYTNGC (SEQ ID NO:5),
CCGGGATCCACAAGCTTCCCTNCAYMRD-GAYATHGC (SEQ ID NO:6),
CCGGGATCCACAAGCTTCCRTNCAYMGN-GAYYTNMG (SEQ ID NO:7),
CCGGGATCCACAAGCTTCCCTNCAYMRD-GAYNTNAA (SEQ ID NO:8),
CCGAATTCACAAGATCTCCNACNC-CNARNSWCCANACRTC (SEQ ID NO:19),
CCGAATTCACAAGATCTCCCAYNCCR-WANGCCCADATRTC (SEQ ID NO:20),
CCGAATTCACAAGATCTCCNACNC-CRAANSWCCACATRTC (SEQ ID NO:21),
CCGAATTCACAAGATCTCCCAYNCCR-WANSWCCANACRTC (SEQ ID NO:9),
CCGAATTCACAAGATCTCCDATNC-CRAANSWCCANSWRTC (SEQ ID NO:10),
CCGAATTCACAAGATCTCCNACNCCR-TANSWCCANGCRTC (SEQ ID NO:11),
CCGAATTCACAAGATCTCCCAYNCCR-WANSWCCADATRCT (SEQ ID NO:12),
CCGAATTCACAAGATCTCCNACNC-CRAANGCCCANACRTC (SEQ ID NO:13),
CCGAATTCACAAGATCTCCNACNC-CRAANGCCCANGTRTC (SEQ ID NO:14),
CCGAATTCACAAGATCTCCCAYNCCR-WANSWCCANACRTC (SEQ ID NO:15),
CCGAATTCACAAGATCTCCCAYNCCR-WANSWRAANACRTC (SEQ ID NO:16), and
oligonucleotides which encode a subset of amino acid residues essentially corresponding to those encoded by the specifically named oligonucleotides;

(b) amplifying said mRNA or cDNA of the biological sample using said pool of oligonucleotides provided in step (a) so that an amplified composition is generated, wherein amplification of nucleic acids encoding said panel of tyrosine kinases reflects their relative expression level within the biological sample, wherein said mRNA or cDNA of the biological sample is extracted and isolated from the biological sample prior to amplification; and (c) assaying the amplified composition for the presence of nucleic acids encoding said panel of tyrosine kinases.

5. The method of claim 4 wherein the oligonucleotide pool comprises at least one oligonucleootide in which inosine replaces at least one wholly degenerate "N."

6. An assay for determining the expression levels of a panel of tyrosine kinases from a biological sample of any species comprising the steps of:

(a) providing a representative pool of oligonucleotides having a sequence which hybridizes to conserved regions in the mRNA or cDNA of said panel of tyrosine kinases, which pool has been tested and determined to provide for the amplification of nucleic acids encoding said panel of tyrosine kinases with essentially the same efficiency;

(b) amplifying said mRNA or cDNA of the biological sample using said pool of oligonucleotides provided in step (a) so that an amplified composition is generated, wherein amplification of nucleic acids encoding said panel of tyrosine kinases reflects their relative expression level within the biological sample; and (c) assaying the amplified composition for the presence of nucleic acids encoding said panel of tyrosine kinases.

7. The assay of claim 6 wherein assay is used to diagnose diseases related to the abnormal expression of at least one tyrosine kinase.

8. The assay of claim 6 wherein the assay is used to monitor a therapeutic treatment for diseases related to the abnormal expression of at least one tyrosine kinase.

9. The assay of claim 6 wherein the assay is used to determine the expression of at least one tyrosine kinase.

10. The assay of claim 6 wherein the assay is used in targeted drug therapy.

11. A method for simultaneously detecting and quantifying the expression of a panel of tyrosine phosphatases from a biological sample of any species comprising the steps of:

(a) providing a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency;

(b) amplifying said mRNA or cDNA of the biological sample using said pool of oligonucleotides provided in step (a) so that an amplified composition is generated, wherein amplification of nucleic acids encoding said panel of tyrosine phosphatases reflects their relative expression level within the biological sample; and (c) assaying the amplified composition for the presence of nucleic acids encoding said panel of tyrosine phosphatases.

12. The method of claim 11 wherein the mRNA or cDNA of the biological sample is extracted and isolated from the biological sample prior to amplification.

13. The method of claim 11 wherein the assay method of step (c) is selected from the group consisting of dot analysis, slot analysis, Northern analysis, and filter hybridization.

14. A method for simultaneously detecting and quantifying the expression of a panel of tyrosine phosphatases from a biological sample of any species comprising the steps of:

(a) providing a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency, wherein the representative pool of oligonucleotides is comprised of the oligonucleotides GAYTTYTGGVRNATGRTNTGGGA (SEQ ID NO:17), and

CGGCCSAYNCCNGCNSWRCARTG (SEQ ID NO:18);

(b) amplifying said mRNA or cDNA of the biological sample using said pool of oligonucleotides provided in step (a) so that an amplified composition is generated, wherein amplification of nucleic acids encoding said panel of tyrosine phosphatases reflects their relative expression level within the biological sample; and (c) assaying the amplified composition for the presence of nucleic acids encoding said panel of tyrosine phosphatases.

15. An assay for determining the expression levels of a panel of tyrosine phosphatases from a biological sample of at least one species comprising the steps of:

(a) providing a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency;

(b) amplifying said mRNA or cDNA of the biological sample using said pool of oligonucleotides provided in step (a) so that an amplified composition is generated, wherein amplification of nucleic acids encoding said panel of tyrosine phosphatases reflects their relative expression level within the biological sample; and (c) assaying the amplified composition for the presence of nucleic acids encoding said panel of tyrosine phosphatases.

16. The assay of claim 15 wherein the assay is used to diagnose diseases related to the abnormal expression of at least one tyrosine phosphatase.

17. The assay of claim 15 wherein the assay is used to monitor a therapeutic treatment for diseases related to the abnormal expression of at least one tyrosine phosphatase.

18. The assay of claim 15 wherein the assay is used to measure the expression of at least one tyrosine phosphatase.

19. The assay of claim 16 wherein the assay is used in targeted drug therapy.

20. The method of claim 4 wherein the mRNA or cDNA of the biological sample is extracted and isolated from the biological sample prior to amplification.

21. The method of claim 4 wherein the assay method of step (c) is selected from the group consisting of dot analysis, slot analysis, Northern analysis and filter hybridization.

22. The method of claim 14 wherein the mRNA or cDNA of the biological sample is extracted and isolated from the biological sample prior to amplification.

23. The method of claim 14 wherein the assay method of step (c) is selected from the group consisting of dot analysis, slot analysis, Northern analysis, and filter hybridization.

24. A kit for simultaneously detecting and quantifying the expression of a panel of tyrosine kinases from a biological sample of any vertebrate species comprising a representative pool of oligonucleotides having a sequence which hybridizes to conserved regions in the mRNA or cDNA of said panel of tyrosine kinases, which pool has been tested and determined to provide for the amplification of said panel of tyrosine kinases with essentially the same efficiency.

25. A kit for simultaneously detecting and quantifying the expression of a panel of tyrosine kinases from a biological sample of any vertebrate species comprising a representative pool of oligonucleotides having a sequence which hybridizes to conserved regions in the mRNA or cDNA of said panel of tyrosine kinases, which pool has been tested and determined to provide for the amplification of nucleic acids encoding said panel of tyrosine kinases with essentially the same efficiency, wherein said representative pool of oligonucleotides is comprised of at least two oligonucleotides selected from the group consisting of:

CCGGGATCCACAAGCTTCCCTNCAYMRD-GAYNTNGC (SEQ ID NO:4),

CCGGGATCCACAAGCTTCCGTNCAYMG-NAAYYTNGC (SEQ ID NO:5),

CCGGGATCCACAAGCTTCCCTNCAYMRD-GAYATHGC (SEQ ID NO:6),

CCGGGATCCACAAGCTTCCRTNCAYMGN-GAYYTNMG (SEQ ID NO:7),

CCGGGATCCACAAGCTTCCCTNCAYMRD-GAYNTNAA (SEQ ID NO:8),

CCGAATTCACAAGATCTCCNACNC-CNARNSWCCANACRTC (SEQ ID NO:19),

CCGAATTCACAAGATCTCCCAYNCCR-WANGCCCADATRTC (SEQ ID NO:20),

CCGAATTCACAAGATCTCCNACNC-CRAANSWCCACATRTC (SEQ ID NO:21),

CCGAATTCACAAGATCTCCCAYNCCR-WANSWCCANACRTC (SEQ ID NO:9),

CCGAATTCACAAGATCTCCDATNC-CRAANSWCCANSWRTC (SEQ ID NO:10),

CCGAATTCACAAGATCTCCNACNCCR-TANSWCCANGCRTC (SEQ ID NO:11),

CCGAATTCACAAGATCTCCCAYNCCR-WANSWCCADATRTC (SEQ ID NO:12),

CCGAATTCACAAGATCTCCNACNC-CRAANGCCCANACRTC (SEQ ID NO:13),

CCGAATTCACAAGATCTCCNACNC-CRAANGCCCANGTRTC (SEQ ID NO:14),

CCGAATTCACAAGATCTCCCAYNCCR-WANSWCCANACRTC (SEQ ID NO:15),

CCGAATTCACAAGATCTCCCAYNCCR-WANSWRAANACRTC (SEQ ID NO:16), and oligonucleotides which encode a subset of amino acid residues essentially corresponding to those encoded by the specifically named oligonucleotides.

26. The kit of claim 25 wherein the oligonucleotide pool comprises at least one oligonucleotide in which inosine replaces at least one wholly degenerate "N."

27. A kit for determining the expression levels of a panel of tyrosine kinases from a biological sample of any species comprising a representative pool of oligonucleotides having a sequence which hybridizes to conserved regions in the mRNA or cDNA of said panel of tyrosine kinases, which pool has been tested and determined to provide for the amplification of nucleic acids encoding said panel of tyrosine kinases with essentially the same efficiency.

28. A kit for simultaneously detecting and quantifying the expression of a panel of tyrosine phosphatases from a biological sample of any species comprising a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency.

29. A kit for simultaneously detecting and quantifying the expression of a panel of tyrosine phosphatases from a biological sample of any species comprising a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency, wherein the representative pool of oligonucleotides is comprised of the oligonucleotides GAYTTYTGGVRNATGRTNTGGGA (SEQ ID NO:17), and

CGGCCSAYNCCNGCNSWRCARTG (SEQ ID NO:18).

30. A kit for determining the expression levels of panel of tyrosine phosphatases from a biological sample of at least one species comprising a representative pool of oligonucleotides having a sequence which hybridizes to conserved regions in the mRNA or cDNA of said panel of tyrosine phosphatases, which pool has been tested and determined to provide for the amplification of nucleic acids encoding said panel of tyrosine phosphatases with essentially the same efficiency.

* * * * *